US009238062B2

(12) United States Patent
Chen et al.

(10) Patent No.: US 9,238,062 B2
(45) Date of Patent: Jan. 19, 2016

(54) HYPOALLERGENIC POLYPEPTIDES FOR THE TREATMENT OF HOUSE DUST MITE ALLERGY

(75) Inventors: Kuan-Wei Chen, Vienna (AT); Susanne Vrtala, Vienna (AT); Rudolf Valenta, Theresienfeld (AT)

(73) Assignee: BIOMAY AG, Vienna (AT)

(*) Notice: Subject to any disclaimer, the term of this patent is extended or adjusted under 35 U.S.C. 154(b) by 106 days.

(21) Appl. No.: 13/990,858

(22) PCT Filed: Nov. 30, 2011

(86) PCT No.: PCT/EP2011/071377
§ 371 (c)(1), (2), (4) Date: Jul. 5, 2013

(87) PCT Pub. No.: WO2012/072678
PCT Pub. Date: Jun. 7, 2012

(65) Prior Publication Data

US 2013/0309261 A1 Nov. 21, 2013

(30) Foreign Application Priority Data

Dec. 1, 2010 (EP) .................................... 10193292

(51) Int. Cl.

| | |
|---|---|
| ***A61K 38/00*** | (2006.01) |
| ***A61K 39/00*** | (2006.01) |
| ***A61K 39/35*** | (2006.01) |
| ***A61K 39/36*** | (2006.01) |
| ***A61K 48/00*** | (2006.01) |
| ***C07H 21/02*** | (2006.01) |
| ***C07H 21/04*** | (2006.01) |
| ***C07K 1/00*** | (2006.01) |
| ***C07K 14/00*** | (2006.01) |
| ***C07K 17/00*** | (2006.01) |
| ***C12N 1/20*** | (2006.01) |
| ***C12N 15/00*** | (2006.01) |
| ***C07K 14/435*** | (2006.01) |

(52) U.S. Cl.
CPC ............. *A61K 39/0003* (2013.01); *A61K 39/35* (2013.01); *C07K 14/43531* (2013.01); *A61K 2039/55566* (2013.01)

(58) Field of Classification Search
None
See application file for complete search history.

(56) References Cited

FOREIGN PATENT DOCUMENTS

WO WO 2009/118642 A2 10/2009

OTHER PUBLICATIONS

Kuby et al. 'Immunology.' Fourth Edition, Chapter 18: 449-465, 2001.*
Mukherjee et al. 'Allergic Asthma: Influence of Genetic and Environmental Factors.' J. Biol. Chem. 38:32883-32889, 2011.*
Laetitia Bussieres et al., "Recombinant Fusion Proteins Assembling Der p 1 and Der p 2 Allergens from Dermatophagoides pteronyssinus", *International Archives of Allergy and Immunology*, 2010, vol. 153, No. 2, pp. 141-151.

* cited by examiner

*Primary Examiner* — Nora Rooney
(74) *Attorney, Agent, or Firm* — Chalin A. Smith; Smith Patent

(57) ABSTRACT

The present invention relates to a polypeptide comprising the amino acid sequence as shown in SEQ ID NO:9 or 7. The invention further pertains to nucleic acids encoding the polypeptide, pharmaceutical compositions and vaccines.

15 Claims, 8 Drawing Sheets

Figure 1B

Construct with Cysteine residues (Der p 2/1C)

```
CATATGATCAAAGACCTGGACGCTTTCCGTCACTACGACGGTCGTACCATCATCCAGCGTGACAACGGTTACCAGCCGAACTACCACGCTGTTAACATCGTTGGTTACTCTAACGCT
 NdeI  I  K  D  L  D  A  F  R  H  Y  D  G  R  T  I  I  Q  R  D  N  G  Y  Q  P  N  Y  H  A  V  N  I  V  G  Y  S  N  A

CAGGGTGTTGACTACTGGATCGTTCGTAACTCTTGGGACACCAACTGGGGTGACAACGGTTACGGTTACTTCGCTGCTAACATCGACCTGATGATGATCGAAGAATACCCGTACGTT
 Q  G  V  D  Y  W  I  V  R  N  S  W  D  T  N  W  G  D  N  G  Y  G  Y  F  A  A  N  I  D  L  M  M  I  E  E  Y  P  Y  V

GTTATCCTGATCAAAGCTTCTATCGAAGGTCTGGAAGTTGACGTTCCGGGTATCGACCCGAACGCTTGCCACTACATGAAATGCCCGCTGGTTAAAGGTCAGCAGTACGACATCAAA
 V  I  L  I  K  A  S  I  E  G  L  E  V  D  V  P  G  I  D  P  N  A  C  H  Y  M  K  C  P  L  V  K  G  Q  Q  Y  D  I  K

TACACCTGGATCGTTCCGAAAATCGCTCCGAAATCTGAAAACGTTGTTGTTACCGTTAAAGTTATGGGTGACAACGGTGTTCTGGCTTGCGCTATCGCTACCCACGCTAAAATCCGT
 Y  T  W  I  V  P  K  I  A  P  K  S  E  N  V  V  V  T  V  K  V  M  G  D  N  G  V  L  A  C  A  I  A  T  H  A  K  I  R

GACCACAACGGTGTTGTTCAGGAATCTTACTACCGTTACGTTGCTCGTGAACAGTCTTGCCGTCGTCCGAACGCTCAGCGTTTCGGTATCTCTAACTACTGCCAGATCTACCCGCCG
 D  H  N  G  V  V  Q  E  S  Y  Y  R  Y  V  A  R  E  Q  S  C  R  R  P  N  A  Q  R  F  G  I  S  N  Y  C  Q  I  Y  P  P

AACGTTAACAAAATCCGTGAAGCTCTGGCTCAGACCCACTCTGCTATCGCTGTTATCATCGGTGACCAGGTTGACGTTAAAGACTGCGCTAACCACGAAATCAAAAAAGTTCTGGTT
 N  V  N  K  I  R  E  A  L  A  Q  T  H  S  A  I  A  V  I  I  G  D  Q  V  D  V  K  D  C  A  N  H  E  I  K  K  V  L  V

CCGGGTTGCCACGGTTCTGAACCGTGCATCATCCACCGTGGTAAACCGTTCCAGCTGGAAGCTGTTTTCGAAGCTAACCAGAACTCTAAAACCGCTAAAATCGAAACCAACGCTTGC
 P  G  C  H  G  S  E  P  C  I  I  H  R  G  K  P  F  Q  L  E  A  V  F  E  A  N  Q  N  S  K  T  A  K  I  E  T  N  A  C

TCTATCAACGGTAACGCTCCGGCTGAAATCGACCTGCGTCAGATGCGTACCGTTACCCCGATCCGTATGCAGGGTGGTTGCGGTTCTTGCTGGGCTTTCTCTGGTGTTGCTGCTACC
 S  I  N  G  N  A  P  A  E  I  D  L  R  Q  M  R  T  V  T  P  I  R  M  Q  G  G  C  G  S  C  W  A  F  S  G  V  A  A  T

GAATCTGCTTACCTGGCTTACCGTAACCAGTCTCTGGACCTGGCTGAACAGGAACTGGTTGACTGCGCTTCTCAGCACGGTTGCCACGGTGACACCATCCCGCGTGGTATCGAATAC
 E  S  A  Y  L  A  Y  R  N  Q  S  L  D  L  A  E  Q  E  L  V  D  C  A  S  Q  H  G  C  H  G  D  T  I  P  R  G  I  E  Y

ATCCAGCACCACCACCACCACCACTAA GAATTC
 I  Q  H  H  H  H  H  H Stop EcoRI
```

Figure 1C

```
Construct with Serine residues (Der p 2/1S)

CATATGATCAAAGACCTGGACGCTTTCCGTCACTACGACGGTCGTACCATCATCCAGCGTGACAACGGTTACCAGCCGAACTACCACGCTGTTAACATCGTTGGTTACTCTAACGCT
 NdeI  I  K  D  L  D  A  F  R  H  Y  D  G  R  T  I  I  Q  R  D  N  G  Y  Q  P  N  Y  H  A  V  N  I  V  G  Y  S  N  A

CAGGGTGTTGACTACTGGATCGTTCGTAACTCTTGGGACACCAACTGGGGTGACAACGGTTACGGTTACTTCGCTGCTAACATCGACCTGATGATGATCGAAGAATACCCGTACGTT
 Q  G  V  D  Y  W  I  V  R  N  S  W  D  T  N  W  G  D  N  G  Y  G  Y  F  A  A  N  I  D  L  M  M  I  E  E  Y  P  Y  V

GTTATCCTGATCAAAGCTTCTATCGAAGGTCTGGAAGTTGACGTTCCGGGTATCGACCCGAACGCTTCTCACTACATGAAATCTCCGCTGGTTAAAGGTCAGCAGTACGACATCAAA
 V  I  L  I  K  A  S  I  E  G  L  E  V  D  V  P  G  I  D  P  N  A  S  H  Y  M  K  S  P  L  V  K  G  Q  Q  Y  D  I  K

TACACCTGGATCGTTCCGAAAATCGCTCCGAAATCTGAAAACGTTGTTGTTACCGTTAAAGTTATGGGTGACAACGGTGTTCTGGCTTCTGCTATCGCTACCCACGCTAAAATCCGT
 Y  T  W  I  V  P  K  I  A  P  K  S  E  N  V  V  V  T  V  K  V  M  G  D  N  G  V  L  A  S  A  I  A  T  H  A  K  I  R

GACCACAACGGTGTTGTTCAGGAATCTTACTACCGTTACGTTGCTCGTGAACAGTCTTCTCGTCGTCCGAACGCTCAGCGTTTCGGTATCTCTAACTACTCTCAGATCTACCCGCCG
 D  H  N  G  V  V  Q  E  S  Y  Y  R  Y  V  A  R  E  Q  S  S  R  R  P  N  A  Q  R  F  G  I  S  N  Y  S  Q  I  Y  P  P

AACGTTAACAAAATCCGTGAAGCTCTGGCTCAGACCCACTCTGCTATCGCTGTTATCATCGGTGACCAGGTTGACGTTAAAGACTCTGCTAACCACGAAATCAAAAAAGTTCTGGTT
 N  V  N  K  I  R  E  A  L  A  Q  T  H  S  A  I  A  V  I  I  G  D  Q  V  D  V  K  D  S  A  N  H  E  I  K  K  V  L  V

CCGGGTTCTCACGGTTCTGAACCGTCTATCATCCACCGTGGTAAACCGTTCCAGCTGGAAGCTGTTTTCGAAGCTAACCAGAACTCTAAAACCGCTAAAATCGAAACCAACGCTTCT
 P  G  S  H  G  S  E  P  S  I  I  H  R  G  K  P  F  Q  L  E  A  V  F  E  A  N  Q  N  S  K  T  A  K  I  E  T  N  A  S

TCTATCAACGGTAACGCTCCGGCTGAAATCGACCTGCGTCAGATGCGTACCGTTACCCCGATCCGTATGCAGGGTGGTTCTGGTTCTTCTTGGGCTTTCTCTGGTGTTGCTGCTACC
 S  I  N  G  N  A  P  A  E  I  D  L  R  Q  M  R  T  V  T  P  I  R  M  Q  G  G  S  G  S  S  W  A  F  S  G  V  A  A  T

GAATCTGCTTACCTGGCTTACCGTAACCAGTCTCTGGACCTGGCTGAACAGGAACTGGTTGACTCTGCTTCTCAGCACGGTTCTCACGGTGACACCATCCCGCGTGGTATCGAATAC
 E  S  A  Y  L  A  Y  R  N  Q  S  L  D  L  A  E  Q  E  L  V  D  S  A  S  Q  H  G  S  H  G  D  T  I  P  R  G  I  E  Y

ATCCAGCACCACCACCACCACCACTAA GAATTC
 I  Q  H  H  H  H  H  H Stop EcoRI
```

HYPOALLERGENIC POLYPEPTIDES FOR THE TREATMENT OF HOUSE DUST MITE ALLERGY

PRIORITY

This application corresponds to the national phase of International Application No. PCT/EP2011/071377 filed Nov. 30, 2011, which, in turn, claims priority to European Patent Application No. 10.193292.9 filed Dec. 1, 2010, the contents of which are incorporated by reference herein in their entirety.

The instant application contains a Sequence Listing that has been submitted in ASCII format via EFS-Web and is hereby incorporated by reference in its entirety. Said ASCII copy, created on May 29, 2013, is named LNK_134_SequenceListing.txt and is 19,438 bytes in size.

FIELD OF THE INVENTION

The present invention deals with the field of immunotherapy against IgE-mediated allergy, particularly house dust mite (HDM) allergy. More specifically the invention relates to the design of a new recombinant hypoallergenic vaccine against HDM allergy

BACKGROUND OF THE INVENTION

House dust mites (HDM) are one of the most important risk factors associated with the development of allergic diseases such as rhinitis, atopic dermatitis and asthma (1, 2) and more than 50% of all allergic patients worldwide suffer from HDM-allergy (3).

So far, 23 different proteins were identified and characterized as HDM allergens (4, 5). Group 1 and group 2 allergens from *Dermatophagoides pteronyssinus* represent the clinically most important HDM allergens with IgE binding frequencies of more than 80% (6-9), and which can be found at high concentrations in mites and in mite feces (10, 11). Allergen-specific immunotherapy (SIT) represents the only causative and disease-modifying approach with long-lasting effects (12-16), which is based on the administration of increasing doses of the disease-eliciting allergens. At present, SIT is performed with natural allergen extracts. But several recent studies have revealed the low quality of natural allergen extracts from pollen, animal dander and house dust mites which may limit clinical efficacy of SIT (17-19). Furthermore, SIT may induce severe side-effects in allergic patients, which limit the broad applicability of this treatment in particular for house dust mite allergy.

Many efforts have been made to engineer recombinant hypoallergenic derivatives in order to improve the safety and efficacy of SIT. And several hypoallergenic derivatives of group 2 mite allergens have already been developed and shown to be suitable for immunotherapy (20-26). In contrast, only a few hypoallergenic derivatives of group 1 mite allergens exist, which are not well characterized (27, 28).

Most strategies using hypoallergenic derivatives can only treat either Der p 1 or Der p 2 allergy and over 50% of HDM-allergic patients react with both allergens, Der p 1 and Der p 2 (29). The advantages of hybrid molecules are that they contain all T-cell epitopes in one molecule and former studies showed that hybrid molecules induce stronger and earlier IgG responses than individual smaller molecules (30, 31).

WO 2009/118642 A2 describes hypoallergenic hybrid proteins composed of fragments of allergens Der p 1 and Der p 2. A similar disclosure can be found in Asturias et al. (2009) Clinical & Experimental Allergy 39, 1088-1098. However, one of the derivatives, i.e., QM1, described in Asturias showed almost the same IgE reactivity as the natural allergen. The second derivative described by Asturias, i.e., QM2, showed reduced IgE reactivity but it is not demonstrated that immunization with this derivative induced IgG antibodies specific for the Der p 1 allergen. Furthermore, the mean inhibition of house dust mite allergic patients IgE by anti-QM2 IgG antibodies to a mix of Der p 1 and Der p 2 was not higher than a 20% mean inhibition.

Bussières et al. (2010) International archives of allergy and immunology 153/2, 141-151 describe studies on recombinant fusion proteins assembling Der p 1 and Der p 2 allergens from *Dermatophagoides pteronyssinus*. These derivatives show no or only a modest reduction of approximately 10 fold of their allergenic activity and it has not been investigated whether immunization with these derivatives induces allergen-specific IgG which inhibits allergic patients IgE binding.

Chen et al. (2008) Molecular Immunology Volume 45, Issue 9, 2486-2498 describes studies on the reduction of allergenicity of Der p 2 by genetic engineering. This derivative includes only Der p 2 but not Der p 1 and therefore cannot be used to treat Der p 1-allergic patients.

The inventors of this application used the hybrid technology to construct a hypoallergenic combination vaccine for immunotherapy of HDM allergy. The two constructed mosaic proteins consisting of fragments derived from Der p 1 and Der p 2. One construct contained the original amino acids of the two wildtype allergens (Der p 2/1C, also referred to herein as Dp 2/1C) whereas in the other construct cysteine residues were replaced with serine residues (Der p 2/1S, also referred to herein as Dp 2/1S). These two mosaic proteins are characterized by an almost complete lack of IgE reactivity and allergenic activity and are therefore different from QM1 described by Asturias and the derivatives described by Bussieres. Both derivatives include all Der p 1 sequence elements and are therefore different from the derivatives described by Chen. IgG antibodies induced by both derivatives (i.e., Der p 2/1C and Der p 2/1S) inhibited allergic patients IgE binding to each of the two allergens, Der p 1 and Der p 2 (Table I), which has not been shown for IgG induced by QM2 made by Asturias.

Unexpectedly, IgG antibodies induced by Der p 2/1S which differs only by the replacement of Cysteine residues to Serine residues, inhibited allergic patients IgE binding to Der p 1 more than double as well as those induced by immunization with Der p 2/1C (See example 6 and the data in Table I). The present invention is therefore specifically directed to the polypeptides comprising the amino acid sequence of Der p 2/1S or substantially the same amino acid sequence.

SUMMARY OF THE INVENTION

A first aspect of the invention is a polypeptide having the amino acid sequence as shown in SEQ ID NO:9 or 7.

Another aspect of the invention is a polynucleotide encoding the polypeptide of this invention.

Yet another aspect of this invention is a vector or plasmid, comprising the polynucleotide of the present invention.

Another aspect of the invention is a pharmaceutical composition comprising the polypeptide of the invention, the polynucleotide of the invention, or the vector or plasmid of the invention; and a pharmaceutically acceptable diluent or excipient.

Another aspect of the invention is the use of the polypeptide of the invention for the prevention and/or treatment of allergy, preferably of house dust mite allergy. The invention also concerns the use of the polypeptide of the invention for the manufacture of a medicament for the prevention and/or treatment of allergy, preferably of house dust mite allergy.

Yet another aspect of the invention is a method of treating and/or preventing an allergic disorder, comprising administering to an individual in need thereof a therapeutically effective amount of the polypeptide or polynucleotide of this invention. Yet another aspect of the invention is a method of treating and/or preventing an allergic disorder, comprising administering to an individual in need thereof a therapeutically effective amount of the pharmaceutical composition or vaccine of this invention.

BRIEF DESCRIPTION OF THE DRAWINGS

FIGS. 1B and C show the codon optimized DNA sequences and the corresponding amino acids of Der p 2/1C (B) and Der p 2/1S(C).

Figure 1A:
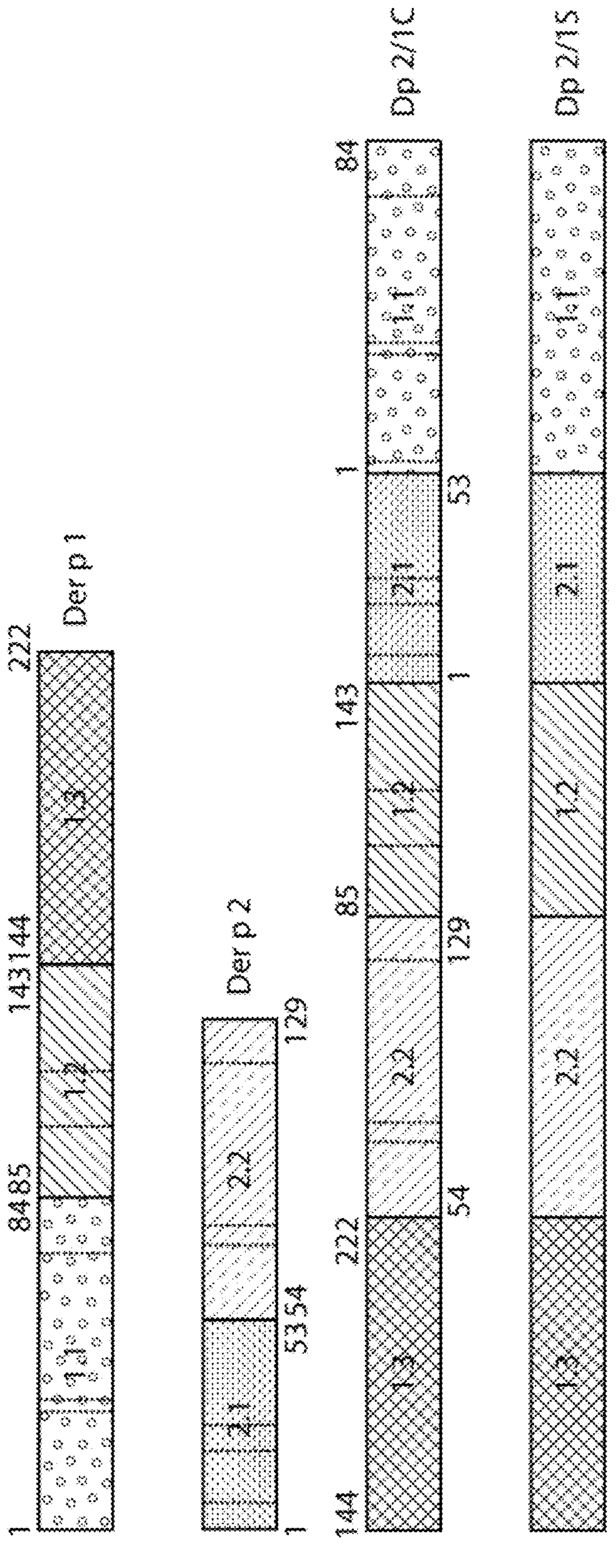
FIG. 1A shows an illustration how Der p 2/1 mosaic proteins were constructed. Three fragments of Der p 1 comprising amino acids (aa) 1-84, aa 85-143 and aa 144-222 (1.1, 1.2 and 1.3) and two fragments of Der p 2 comprising aa 1-53 and aa 54-129 (2.1 and 2.2) were reassembled in the order 1.3, 2.2, 1.2, 2.1, 1.1. Dp 2/1C contains the original aa sequence of Der p 1 and Der p 2 with twelve cysteine-residues (dashed lines), in Dp 2/1S the cysteine-residues were exchanged with serine-residues.

Table I shows the Inhibition of allergic patients' IgE binding to nDer p 1 and rDer p 2 with rabbit anti-Der p 1, anti-Der p 2 or anti-Der p 2/1 antisera. The results are indicated in % inhibition of IgE-binding.

DETAILED DESCRIPTION OF THE INVENTION

Polypeptides of the Invention

The polypeptide of the invention comprises the amino acid sequence as shown in SEQ ID NO:9 or substantially the same amino acid. The term "substantially the same" refers to variants having from 1 to 5 amino acid substitutions relative to SEQ ID NO:9, but having substantially the same biological activity.

The polypeptide of this invention does not necessarily consist only of amino acid sequences derived from the allergens. It is possible that non-native sequences (e.g. spacer sequences) are inserted between the fragments (which fragments are consecutive amino acid sequences from Der p 1 and Der p 2). It is also possible that the polypeptides comprise a tag sequence which facilitates the purification of the polypeptide upon expression in a host cell. A "tag", as used herein, refers to a distinct amino acid sequence that can be used to detect or purify the provided polypeptide, wherein the tag does not otherwise contribute to the essential function of the composition. Examples of such tag sequences include but are not limited to FLAG tag, Hemagglutinin (HA) tag, myc-tag and polyhistidine tag. Other tags are known to those of skill in the art. The preferred tag is a hexahistidine tag which allows purification by $Ni^{2+}$ chelate chromatography. Furthermore, the polypeptide may contain a foreign methionine residue at amino acid position 1 which results from expression in host cells. The methionine will often be present if the N-terminal portion of the polypeptide is an internal or C-terminal allergen fragment. The provided polypeptide can further have deleted N-terminal, C-terminal or intermediate amino acids that do not contribute to the essential activity of the polypeptide.

The hypoallergenic polypeptide may comprise or consist of any one of the following structures (I) to (VIII), written from N- to C-terminal:

(I) Met-X-tag,
(II) Met-X,
(III) X-tag,
(IV) Met-tag-X,
(V) tag-X,
(VI) tag-X-tag,
(VII) X
(VIII) Met-tag-X-tag wherein Met is an N-terminal methionine residue, X is the amino acid sequence as shown in SEQ ID NO:9, and tag is a peptide tag sequence (e.g. $(His)_6$). The tag sequence usually is 5 to 15 amino acids in length.

The polypeptide may consist of an amino acid sequence selected from the group consisting of SEQ ID NOs:7 and 9.

Determination of IgE Reactivity

The polypeptide of the invention preferably has a reduced IgE reactivity relative to Der p 1 and/or Der p 2. In a broad sense, the phrase "IgE reactivity" denotes the capability of a substance to bind to IgE antibodies. More specifically, as used herein, the phrase "IgE reactivity" refers to the capability of the polypeptide to bind to IgE antibodies from individuals that are allergic against one or more of the allergens from which the fragments within the polypeptide are derived.

IgE reactivity may be measured by determining the degree of binding between (1) serum IgE from individuals that are allergic against one or more of Der p 1 and Der p 2, and (2) the polypeptide. This may be done by the method described in reference (26).

Alternatively, IgE reactivity and allergenic activity may be determined by analysing the expression of CD203c on human basophils that were isolated from individuals allergic to one or more of Der p 1 and Der p 2. See example 4 and reference (32).

Determination of T Cell Reactivity

The polypeptide preferably has T cell reactivity. The phrase "T cell reactivity" as used herein refers to the capability of a substance to specifically bind to T cell receptors. More specifically, "T cell reactivity" means the capability of the polypeptide to induce proliferation of T cells.

The T cell reactivity of the polypeptides can be measured by (1) providing peripheral blood mononuclear cells (PBMCs) isolated from individuals allergic against one or more of the allergens from which the fragments are derived, and (2) determining the degree of proliferation of T cells contained in said PBMCs. See Ball et al. (2009) *Allergy* 64:569-80.

Induction of a Protective IgG Response

The polypeptide of the invention preferably has the capability to induce an IgG response against one or more of the allergens from which the fragments are derived. This may be determined by (1) immunizing a non-human mammal (e.g. a mouse, rat or rabbit) with the polypeptide, and (2) determining the amount of IgG antibodies raised in said non-human mammal, which are specific to said one or more allergen(s) from which the fragments are derived. The IgG antibodies measured are preferably IgG1 antibodies. Preferably, step (2) is performed using an ELISA assay. See example 5.

The polypeptides are preferably capable of inducing a protective IgG response. This may be determined by (1) providing a composition containing IgG antibodies by immunizing a non-human mammal (e.g. a mouse, rat or rabbit) with the polypeptide; (2) providing a composition containing IgE antibodies from individuals that are allergic against one or more of said allergens from which the fragments of the polypeptide are derived, and (3) measuring whether and/or to which extent said composition containing IgG antibodies can block the binding of said IgE antibodies to one or more of said allergens.

This test is preferably performed using an ELISA assay. For example, the wild type allergens from which the fragments are derived may be immobilized on an ELISA plate. The thus pre-treated ELISA plate may then be contacted with said composition containing the IgG antibodies to allow binding of IgG antibodies to said immobilized allergens. After washing the composition containing said IgE antibodies is contacted with the ELISA plate. After washing the amount of IgE antibodies are determined. See Example 6.

Further Aspects of the Invention

The invention further concerns a polynucleotide encoding the polypeptide of the present invention. Due to the degeneracy of the genetic code many different polynucleotide molecules may encode a single polypeptide. The polynucleotide of the invention preferably is an expression construct for obtaining the polypeptide after expression in host cells. The expression construct may further comprise components which are generally known in the art such as promoter sequences, genes encoding resistance factors against antibiotics, a replication origin and the like. Preferably, the polynucleotide comprises the nucleic acid sequence as shown in SEQ ID NO:10. More preferably, the polynucleotide comprises the nucleic acid sequence as shown in SEQ ID NO:8.

The invention further concerns a cell transfected or transformed with a polynucleotide of the present invention. Suitable cells include eukaryotic cells and prokaryotic cells. Eukaryotic cells may be transfected by methods known in the art such as calcium phosphate mediated transfection, electroporation, lipofection etc.

The invention further relates to a pharmaceutical composition or vaccine containing the polypeptide, polynucleotide or cell according to this invention. The pharmaceutical composition may further contain one or more pharmaceutically acceptable carrier(s) or diluents(s) such as a buffer or salt solution. Preferably the pharmaceutical composition of the invention is a vaccine composition. In a particular embodiment the pharmaceutical composition further contains an adjuvant such as aluminium hydroxide.

The invention also relates to a method for the preparation of the polypeptide of the invention. The method comprises providing a polynucleotide encoding the polypeptide, introducing said polynucleotide into a host cell, culturing the host cell thus obtained under conditions such that the hybrid polypeptide is expressed, in recovering the expression product from the cell. The polynucleotide may be prepared by methods known in the art. It may be preferred that PCR technology is used to prepare the polynucleotide encoding the polypeptide of the invention.

The invention further relates to the use of the polypeptide, a polynucleotide or a cell described herein for the preparation of a medicament for the treatment and/or prevention of an allergic disorder, preferably of house dust mite allergy. Such a medicament may be composed of the polynucleotide encoding a vaccine which can be used directly for the DNA-based vaccination against Type 1 allergy. The recombinant or synthetic polypeptide may be used to prepare formulations for the oral, sublingual or parenteral treatment of Type 1 allergic disorders as they are now routinely used for immunotherapy. Examples of formulations for sublingual immunotherapy or adjuvant bound hybrid polypeptide for injection immunotherapy. Possible applications include also cell-based forms of immunotherapy which may be based on e.g. dendritic cells or other antigen presenting cells. Those cells are transformed and expressed to antigen in vivo. Preferably orthologous cells transformed with suitable vectors are used.

One mode of application may be the subcutaneous injection of adjuvant-bound polypeptide. Another possibility is oral or nasal administration of the polypeptide in order to induce immunological tolerance or anergy against the components of the polypeptide. All the possible formulations can be prepared according to measures which are known to those of skill in the art (dosage adjuvants scheme of administration).

The invention further relates to the use of the polypeptide described herein or of a polypeptide or a cell described herein for the preparation of a medicament for prophylactic vaccination or tolerance induction. Prophylactic administration of hybrid polypeptides means the administration of the polypeptide to individuals, preferably children who do not yet suffer from Type 1 allergy in order to induce a state of immunological tolerance, anergy or non-responsiveness, or a protective immunity against the components of the hybrid vaccine. This may be achieved by the various protocols outlined for treatment of an established allergic disorder. The prophylactic treatment may be performed with the polypeptides or polynucleotides described herein above.

In a further embodiment the invention relates to the use of a polypeptide described herein for the detection of antibodies against an allergenic protein in a sample. The antibody may be an IgM IgE, IgG or IgA antibody. The concentration of the antibody may be determined from a sample which has been obtained from a body fluid. The sample may be derived from animals or humans. Such tests may rely on a solid phase immobilized polypeptide or the polypeptide in the fluid phase. Examples for such tests include ELISA tests, Western blotting tests or any other tests where the polypeptide is immobilized to bind to specific antibodies out from the sample. Alternatively the polypeptide is added directly to the antibody containing fluid in order to adsorb specific antibodies as, e.g., in competitive immunological assays.

The polypeptide of the invention may also be used for cellular tests such as a T cell proliferation test, etc.

Summary of the Amino Acid and Nucleotide Sequences Shown in the Sequence Listing:

| SEQ ID NO: | sequence / construct |
|---|---|
| 1 | amino acid sequence of mature (i.e. without signal sequence and propeptide) wild type Der p 1 with N-terminal methionine |
| 2 | amino acid sequence of wild type Der p 2 with 2 foreign amino acids at the N-terminus and a hexahistidine tag at the C-terminus; this construct was used in the examples |
| 3 | DNA sequence encoding SEQ ID NO: 1 |
| 4 | DNA sequence encoding SEQ ID NO: 2 |
| 5 | amino acid sequence of construct Dp 2/1C |
| 6 | nucleic acid sequence encoding SEQ ID NO: 5 |
| 7 | amino acid sequence of construct Dp 2/1S |
| 8 | nucleic acid sequence encoding SEQ ID NO: 7 |
| 9 | amino acid sequence of construct Dp 2/1S without C-terminal $(His)_6$ |
| 10 | nucleic acid sequence encoding SEQ ID NO: 9 |
| 11 | amino acid sequence of hexahistidine tag |

The following examples further illustrate the invention. The scope of the invention, however, is not limited to the examples.

EXAMPLES

Example 1

Construction of Der p 2/1 Mosaic Proteins

To construct the Der p 2/1 mosaic protein, three fragments of Der p 1 (1.1 aa1-84; 1.2 aa 85-143; 1.3 aa144-222) and two fragments of Der p 2 (2.1 aa 1-53; 2.2 aa 54-129) were reassembled in the following order: 1.3, 2.2, 1.2, 2.1, 1.1 (FIG. 1A). Two synthetic genes for the Der p 2/1 mosaic proteins were synthesized with a C-terminal hexahistidines tag and codon-optimized for the expression in *E. coli* (ATG biosynthetics, Merzhausen, Germany). One gene contained the DNA coding for the original Der p 1 and Der p 2 aa sequence with the twelve cysteine-residues (Dp 2/1C) (FIG. 1B) and in the other gene, the cysteine-residues were exchanged with serine-residues (Dp 2/1S) (FIG. 1C). The synthetic genes were cloned into the NdeI/EcoRI fragment of the multiple cloning site of the expression vector pET17b and the DNA sequences were determined by sequencing (ATG biosynthetics).

Example 2

Expression and Purification of Der p 2/1 Mosaic Proteins

Expression vectors containing the Der p 2/1 constructs were transformed into *E. coli* strain BL21 (DE3). Protein expression was performed in 250 ml liquid culture by induction with 0.5 mM isopropyl-β-thiogalactopyranoside (IPTG) at an $OD_{600}$ of 0.8 for 4 h at 37° C. and cells were harvested by centrifugation at 4000×g for 15 min at 4° C. The bacterial pellets obtained from 250 ml liquid culture were resuspended in 10 ml 25 mM imidazol, pH 7.4, 0.1% (v/v) Triton X-100. Cells were lysed by three freeze/thawing cycles (−70° C./+50° C.), DNA was degraded by incubation with 1 μg DNase I for 10 min at room temperature and cell debris were removed by centrifugation (10,000×g, 30 min, 4° C.). Dp2/1C and Dp 2/1S mosaic proteins were found in the pellet in the inclusion body fraction, which was solubilised with 6M guanidine hydrochloride, 100 mM $NaH_2PO_4$, 10 mM Tris-Cl, pH 8 for 4 h at room temperature. Insoluble residues were removed by centrifugation (10,000×g, 15 min, 4° C.) and the two mosaic proteins were purified under denaturing conditions over Ni-NTA resin affinity columns (QIAGEN, Hilden, Germany).

Fractions, containing recombinant proteins of more than 90% purity were dialysed against 10 mM $NaH_2PO_4$, pH 4.7 and the final protein concentrations were determined by BCA Protein Assay Kit (Novagen, Merck, Darmstadt, Germany).

Example 3

Characterization of Der p 2/1 Mosaic Proteins

Figure 2:
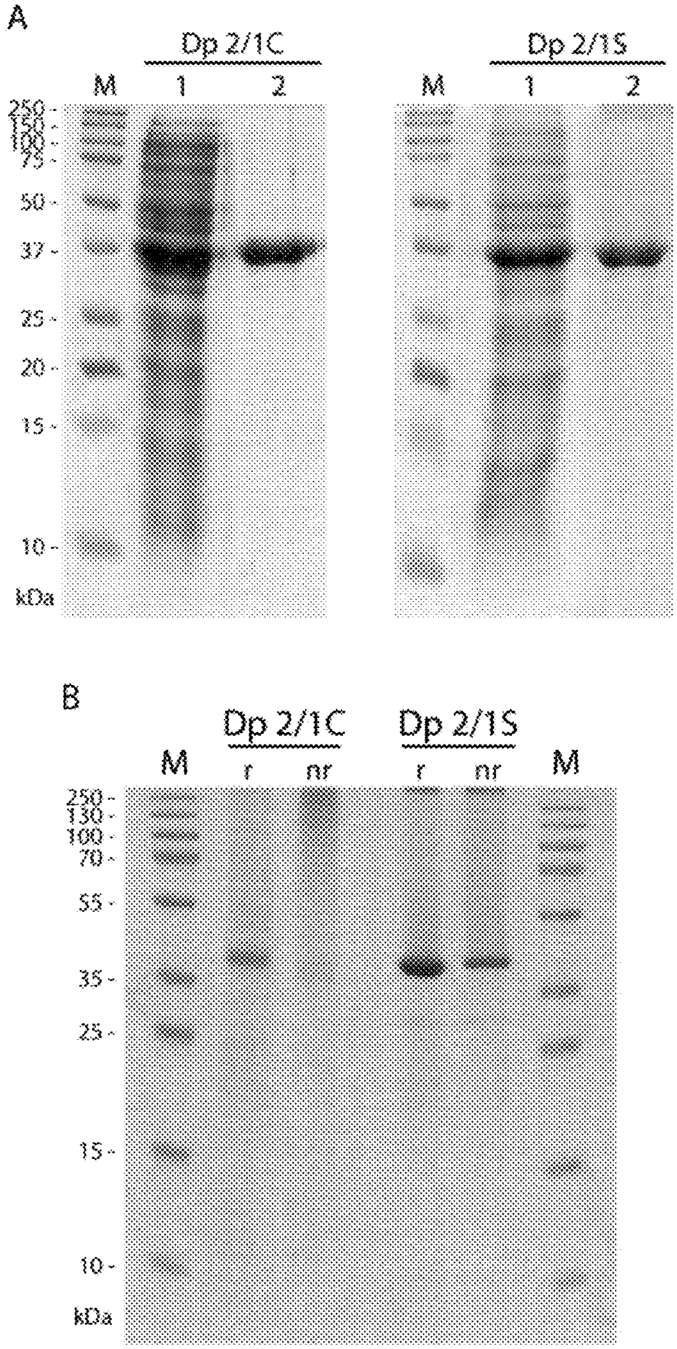
FIG. 2 shows a Coomassie-stained SDS-PAGE gel with expressed (lanes 1) and purified (lanes 2) Der p 2/1C and Der p 2/1S mosaic proteins (A). And a Coomassie-stained SDS-PAGE gel containing purified Der p 2/1C and Der p 2/1S separated under reducing (lanes r) and non-reducing condition (lanes nr) and a molecular marker (lanes M) (B).

The purity and molecular mass was controlled by SDS-PAGE shown in FIG. 2A. Both mosaic proteins show a clear band at approximately 37 kDa. To achieve information about polymerization behaviour of the mosaic proteins SDS-PAGE was performed under reducing and non-reducing conditions shown in FIG. 2B. For reducing conditions a sample buffer containing β-Mercaptoethanol was used and samples were boiled at 95° C. for 5 minutes, for non-reducing conditions a sample buffer with out β-Mercaptoethanol was used. Under reducing conditions the two Der p 2/1 mosaic proteins appear as monomeric proteins (FIG. 2B, lanes r). But under non-reducing conditions the two Der p 2/1 mosaic proteins form aggregates, whereas Der p 2/1C forms more aggregates than Der p 2/1S (FIG. 2B, lanes nr).

Figure 3:
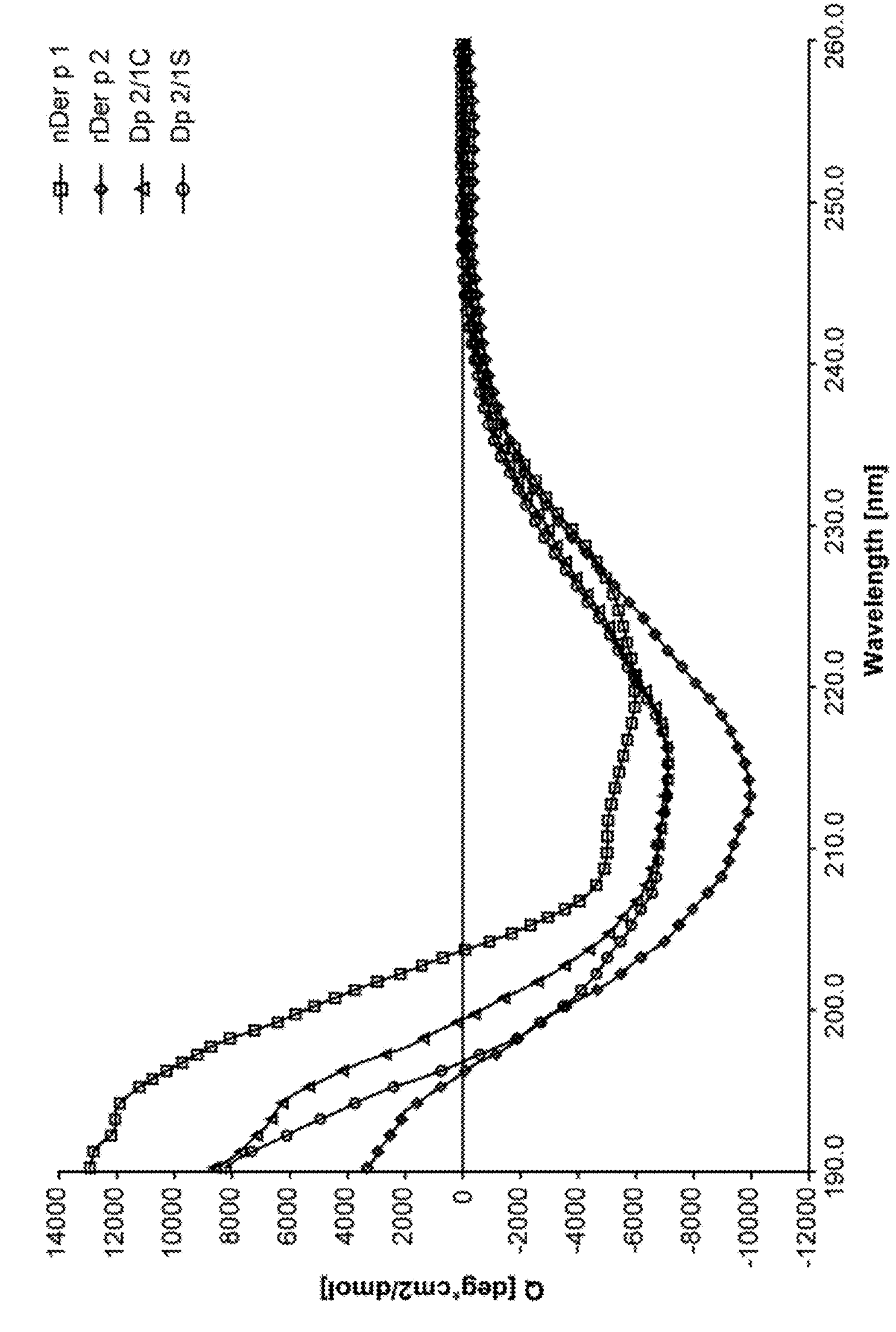
FIG. 3 shows the far-ultraviolet CD spectra of nDer p 1, rDer p 2 and Dp 2/1 mosaic proteins. Results of the far-UV CD analysis of the proteins are expressed as mean residue ellipticities (y-axis) at given wavelengths (x-axis).

To analyse the protein fold, Circular dichroism (CD) measurements were performed with nDer p 1, rDer p 2, Der p 2/1C and with Der p 2/1S at protein concentrations of 0.1 mg/ml in 10 mM $NaH_2PO_4$, pH 4.7 using a rectangular quartz cuvette with a path length of 0.2 cm. Spectra were recorded from 190 to 260 nm with 0.5 nm resolution at a scan speed of 50 nm/min and resulted from averaging of three scans. The final spectra were corrected by subtracting the baseline spectra obtained with the corresponding buffer (10 mM $NaH_2PO_4$, pH 4.7) under identical conditions. Results are expressed as the mean residue ellipticity (Θ) at a given wavelength. The CD spectrum of nDer p 1 indicated a high content α-helix, which is characterized by a minimum at 208 nm and at 222 nm (FIG. 3). The rDer p 2 CD spectrum exhibits a minimum at 215 nm and a maximum at 197 nm, which is typical for β-sheet conformation (FIG. 3). The CD spectra of Der p 2/1C and Der p 2/1S are very similar exhibiting a broad minimum at 215 nm and a maximum at 195 nm, which is a typical shape for a mixed α/β-fold (FIG. 3).

Example 4

IgE Reactivity and Allergenic Activity of the Der p 2/1 Mosaic Proteins

Figure 4:
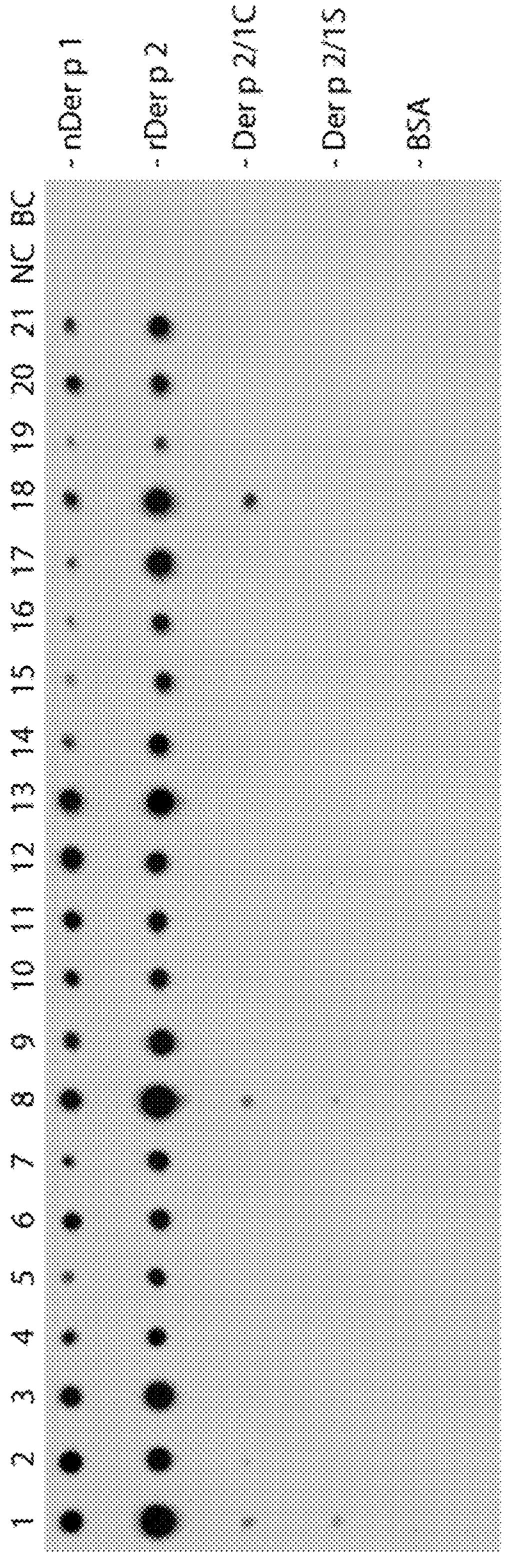
FIG. 4 shows the IgE reactivity of nDer p 1, rDer p 2 and Dp 2/1 mosaic proteins. Dot-blotted nDer p 1, rDer p 2, the two Dp 2/1 mosaic proteins and BSA were tested for IgE reactivity with sera from 21 HDM-allergic patients (patient 1-21), serum from a non-allergic individual (NC) and buffer without serum (BC). Bound IgE were detected with $^{125}$I labeled anti-human IgE antibodies and visualized by autoradiography.

IgE reactivity of mite allergic patients to Der p 2/1 mosaic proteins was tested by dot blot analysis shown in FIG. 4. 2 μl of nDer p 1, rDer p 2, the two mosaic proteins (Der p 2/1C and Der p 2/1S) and, for control purposes, BSA (each 0.1 mg/ml) were dotted onto nitrocellulose membrane strips. IgE reactivity of 21 mite allergic patients and two controls (NC: non-allergic person, BC: buffer control) to the dot-blotted proteins was determined as described (26). All allergic patients showed a positive IgE reactivity to nDer p 1 and rDer p 2, whereas only three patients (patient 1, 8, and 19) showed IgE reactivity to Der p 2/1C and two patients (patient 1 and 8) showed reduced IgE reactivity to Der p 2/1S. All other patients showed no detectable IgE reactivity to Der p 2/1C and Der p 2/1S. When serum from a non-allergic person (NC) or buffer without serum (BC) was used, no reactivities to any dotted proteins were found (FIG. 4, lanes NC, BC). None of the patients showed any IgE reactivity to the control protein, BSA (FIG. 4).

Figure 5:
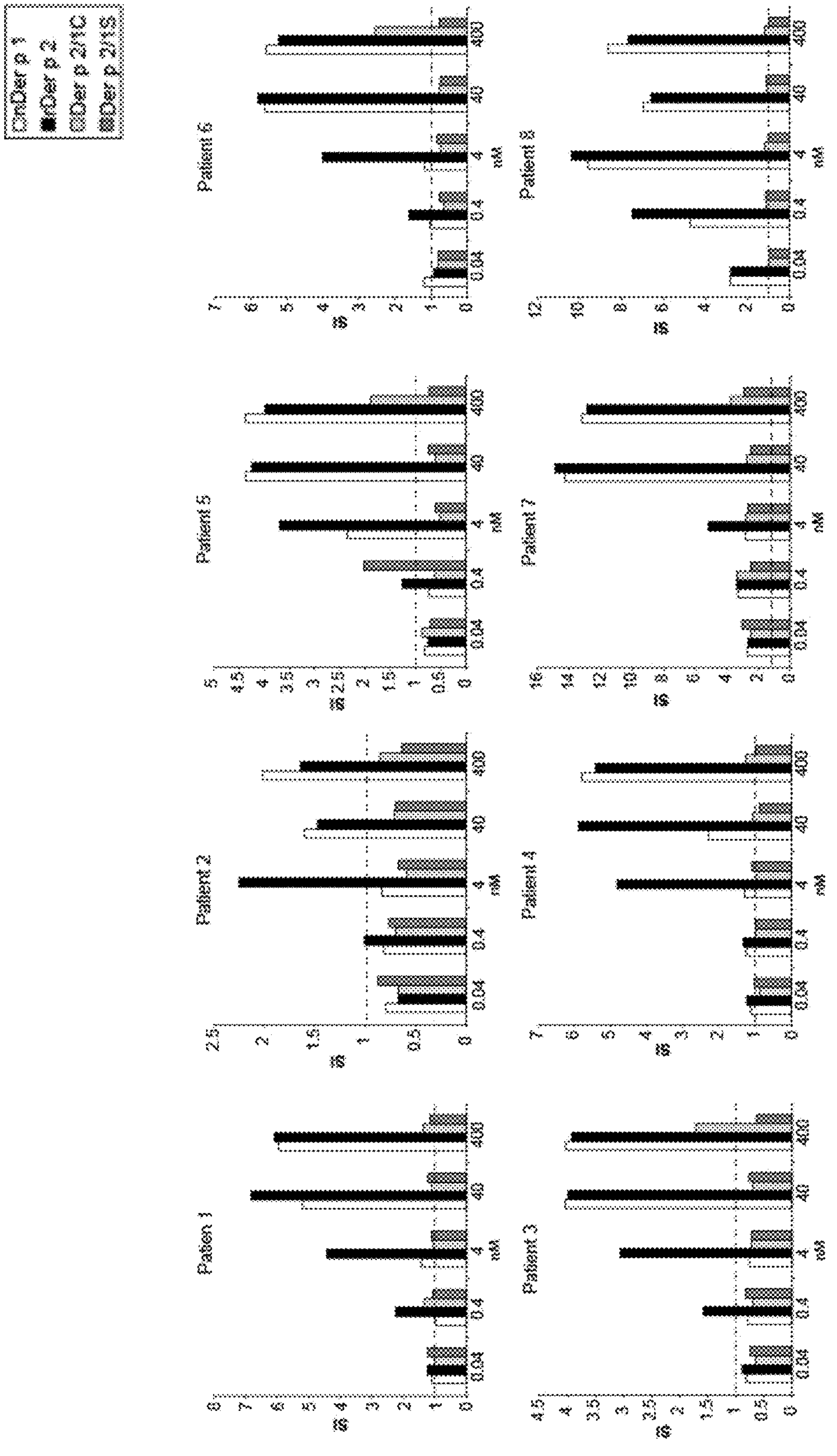
FIG. 5 shows the allergenic activity of Der p 1, Der p 2 and Der p 2/1 mosaic proteins. Basophils from 8 mite allergic patients were stimulated with various concentrations of nDer p 1, rDer p 2, Der p 2/1C and Der p2/1S (x-axes). Expression of CD203c was determined by FACS analysis and is displayed as stimulation index (SI) (y-axes).

The allergenic activity of the two Der p 2/1 mosaic proteins was compared with nDer p 1 and rDer p 2 wildtype allergens by determine CD203c expression on basophils from 8 HDM-allergic patients, when stimulated with the two wildtype allergens or the two Der p 2/1 mosaic proteins shown in FIG. 5. Heparinized blood samples from 8 mite allergic patients were collected after informed consent was given. Basophils were stimulated with various concentrations (0.04-400 nM) of nDer p 1, rDer p 2, Der p 2/1C and Der p 2/1S, and for control purposes, with a monoclonal anti-IgE antibody (1 μg/ml) or PBS for 15 min (37° C.). Expression of CD203c was determined as described (32). These analyses showed that both wildtype allergens nDer p 1 and rDer p 2 induced strong up-regulation of CD203c expression in all tested HDM-allergic patients at concentrations between 0.4 nM and 400 nM, whereas no relevant up-regulations were obtained with Der p 2/1C and Der p 2/1S mosaic proteins up to a concentration of 400 nM. Anti-human IgE antibodies were used as positive control and induced up-regulation of CD203c expression on basophils from all patients, whereas no up-regulation was obtained with buffer alone (Data not shown).

Example 5

Immunization of Rabbits with the Two Der p 2/1 Mosaic Proteins

Figure 6:
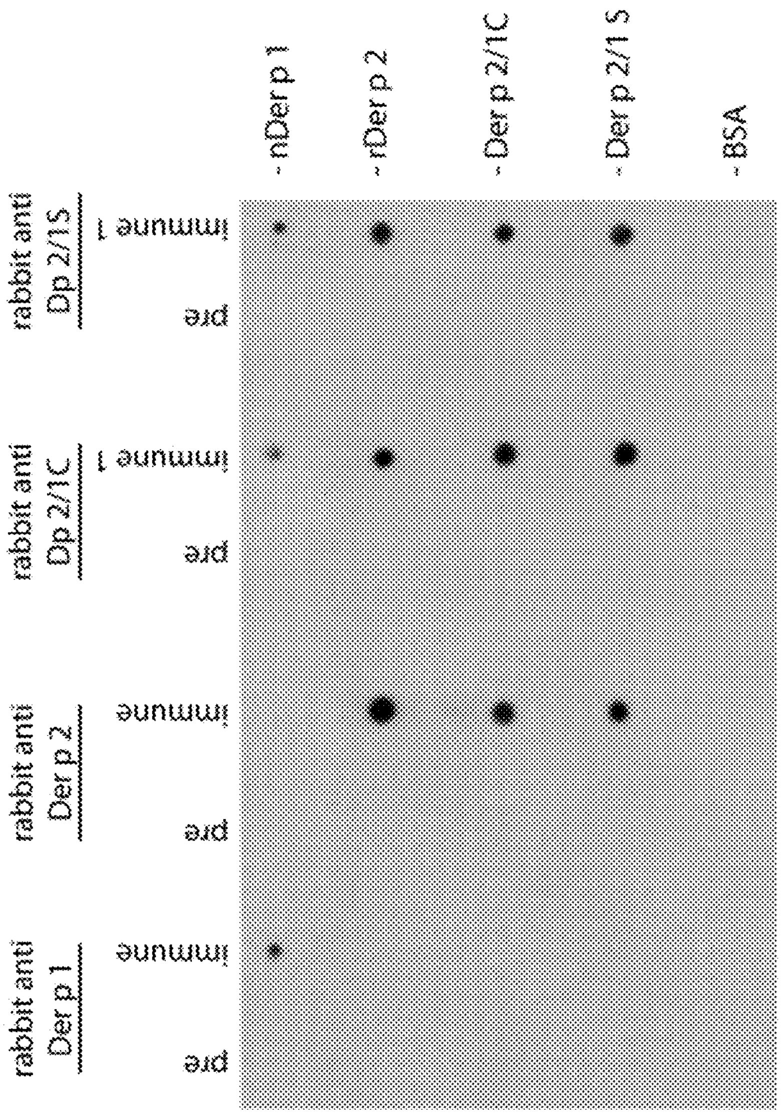
FIG. 6 shows the IgG antibody responses induced by immunization of rabbits with Der p 1, Der p 2 and Dp2/1 mosaic proteins. Sera obtained from rabbits before (pre) or after (immune) immunization with nDer p 1, rDer p 2, Der p 2/1C and Der p 2/1S were tested for IgG reactivity to dot-blotted nDer p 1, rDer p 2, Der p 2/1 mosaic proteins or BSA. Bound IgG antibodies were detected with $^{125}$I-labeled donkey anti-rabbit IgG antibodies.

To demonstrate whether the two mosaic proteins are able to induce specific Der p 1 and Der p 2 IgG antibodies, rabbits were immunized five times either with Der p 2/1C or with Der p 2/1S (200 μg/injection), using CFA for the first immunization and four times IFA as adjuvants. Additionally, rabbits were immunized three times with nDer p 1 or rDer p 2 (200 μg/injection) using once Freund's complete (CFA) and two times Freund's incomplete adjuvants (IFA) to raise specific IgG antibodies against the two wild type allergens. Both Der p 2/1 mosaic proteins were able to induce Der p 1 and Der p 2 specific IgG antibodies (FIG. 6). For control purposes, anti-Der p 1 and anti-Der p 2 rabbit sera were used. Anti-Der p 1 rabbit serum reacted positive only with dotted nDer p 1, whereas anti-Der p 2 rabbit serum reacted positive with rDer p 2 and also with the two Der p 2/1 mosaic proteins (FIG. 6). None of the rabbit sera showed any reactivity to the control protein, BSA (FIG. 6).

Example 6

Inhibition of Allergic Patients' IgE Binding to nDer p 1 and rDer p 2 by Rabbit Anti-Der p 2/1C and Rabbit Anti-Der P 2/1S Antibodies We investigated whether IgG antibodies induced by Der p 2/1 mosaic proteins are able to inhibit HDM-allergic patients' IgE binding to nDer p 1 and rDer p 2 in ELISA competition experiments.

Maxisorp ELISA plates (Nunc) were coated overnight at 4° C. with nDer p 1 or rDer p 2 (0.5 μg/well in PBS), washed twice with PBST (PBS; 0.05% [v/v] Tween 20) and then blocked in blocking buffer (PBST, 1% [w/v] BSA) for 3 h at room temperature. Rabbit anti-nDer p 1, rDer p 2, Der p 2/1C and rabbit anti-Der p 2/1S antisera (1:20 dilution in PBST, 0.5% (w/v) BSA), and the corresponding preimmunesera (1:20 dilution in PBST, 0.5% (w/v) BSA) were added onto the plates and incubated overnight at 4° C. After washing, the plates were incubated with mite allergic patients' sera (1:10 dilution in PBST, 0.5% (w/v) BSA) overnight at 4° C. Bound human IgE antibodies were detected with HRP-coupled goat anti-human IgE antibodies (KPL, Gaithersburg, Md., USA) diluted 1:2500 in PBST, 0.5% (w/v) BSA as described (33). The percentage inhibition of IgE binding was calculated as follows: 100−(ODs/ODp)×100. ODs and ODp represent the extinctions after preincubation with the rabbit immune serum and preimmune serum, respectively.

Rabbit anti-Der p 1 antibodies inhibited patients' IgE binding to nDer p 1 between 49.1% and 91.8% (mean 74.9%). The inhibitions to nDer p 1 obtained with rabbit anti-Der p 2/1C (i.e., 0-48.7%; mean 24.1%) and with rabbit anti-Der p 2/1S (i.e., 31.9-66.0%; mean 49.9%) were lower compared to rabbit anti-Der p 1. Using rabbit anti-Der p 2 antibodies inhibited patients' IgE binding to rDer p 2 between 50.3% and 92.9% (mean 73.9%) and inhibition with rabbit anti-Der p 2/1C (i.e., 56.9-93.4%; mean 78.1%) and with rabbit anti-Der p 2/1S (i.e., 73-93.3%; mean 86.1%) were comparable with rabbit anti-Der p 2 antibodies (Table I).

TABLE I

Inhibition of allergic patients' IgE binding to nDer p 1 and rDer p 2 with rabbit anti-Der p 1, anti-Der p 2 or anti-Der p 2/1 antisera.

| | inhibition to nDer p 1 | | | inhibition to rDer p 2 | | |
|---|---|---|---|---|---|---|
| | nDer p 1 | Rabbit anti-Der p 2/1C | Der p 2/1S | rDer p 2 | Rabbit anti-Der p 2/1C | Der p 2/1S |
| Patient 1 | 89.58 | 19.09 | 44.97 | 75.46 | 81.73 | 87.16 |
| Patient 2 | 88.09 | 41.54 | 56.23 | 92.20 | 93.35 | 94.30 |
| Patient 3 | 61.12 | 1.25 | 38.10 | 67.08 | 72.44 | 83.21 |
| Patient 4 | 72.28 | 35.68 | 59.61 | 69.94 | 71.64 | 82.09 |
| Patient 5 | 76.79 | 45.17 | 54.16 | 92.93 | 92.35 | 93.04 |
| Patient 6 | 89.30 | 43.06 | 61.66 | 80.89 | 85.07 | 90.28 |
| Patient 7 | 49.12 | 0.00 | 35.17 | 61.98 | 69.39 | 80.65 |
| Patient 8 | 58.05 | 0.00 | 31.92 | 59.21 | 64.62 | 78.48 |
| Patient 9 | 82.53 | 20.15 | 51.54 | 69.23 | 77.31 | 88.79 |
| Patient 10 | 91.78 | 48.72 | 65.99 | 88.12 | 89.86 | 93.47 |
| Patient 11 | 57.88 | 4.16 | 43.82 | 50.34 | 56.90 | 72.97 |
| Patient 12 | 82.10 | 30.41 | 55.72 | 79.37 | 82.59 | 88.31 |
| mean | 74.89 | 24.10 | 49.91 | 73.90 | 78.10 | 86.06 |

Results are shown in % inhibition of IgE-binding

Example 7

The skilled person is aware that hypoallergenic polypeptides corresponding to those described above in Examples 1-6 can be prepared on the basis of variants of Der p 1 and Der p 2. The accession numbers of various isoallergens of Der p 1 and Der p 2 are provided in the following tables:

TABLE II

| Der p 1 isoallergen | GenBank accession No. Nucleotide | UniProt accession No. |
|---|---|---|
| Der p 1.0101 | U11695 (variant) | P08176 (variant) |
| Der p 1.0102 | U11695 | P08176 |
| Der p 1.0103 | U11695 (variant) | P08176 (variant) |
| Der p 1.0104 | U11695 (variant) | P08176 (variant) |
| Der p 1.0105 | U11695 (variant) | P08176 (variant) |
| Der p 1.0106 | U11695 (variant) | P08176 (variant) |
| Der p 1.0107 | U11695 (variant) | P08176 (variant) |
| Der p 1.0108 | U11695 (variant) | P08176 (variant) |
| Der p 1.0109 | U11695 (variant) | P08176 (variant) |
| Der p 1.0110 | U11695 (variant) | P08176 (variant) |
| Der p 1.0111 | U11695 (variant) | P08176 (variant) |
| Der p 1.0112 | U11695 (variant) | P08176 (variant) |
| Der p 1.0113 | DQ185508 (variant) | Q3HWZ5 (variant) |

TABLE II-continued

| Der p 1 isoallergen | GenBank accession No. Nucleotide | UniProt accession No. |
|---|---|---|
| Der p 1.0114 | DQ185508 (variant) | Q3HWZ5 (variant) |
| Der p 1.0115 | DQ185508 (variant) | Q3HWZ5 (variant) |
| Der p 1.0116 | DQ185508 (variant) | Q3HWZ5 (variant) |
| Der p 1.0117 | DQ185508 (variant) | Q3HWZ5 (variant) |
| Der p 1.0118 | DQ185508 (variant) | Q3HWZ5 (variant) |
| Der p 1.0119 | DQ185508 (variant) | Q3HWZ5 (variant) |
| Der p 1.0120 | DQ185508 (variant) | Q3HWZ5 (variant) |
| Der p 1.0121 | DQ185508 (variant) | Q3HWZ5 (variant) |
| Der p 1.0122 | DQ185508 (variant) | Q3HWZ5 (variant) |
| Der p 1.0123 | DQ185508 (variant) | Q3HWZ5 (variant) |
| Der p 1.0124 | FM177224 | |

TABLE III

| Der p 2 isoallergen | GenBank accession No. Nucleotide | UniProt accession No. |
|---|---|---|
| Der p 2.0101 | AF276239 | P49278 |
| Der p 2.0102 | AF276239 | P49278 |
| Der p 2.0103 | AF276239 | P49278 |
| Der p 2.0104 | AF276239 | P49278 |
| Der p 2.0105 | AF276239 | P49278 |
| Der p 2.0106 | AF276239 | P49278 |
| Der p 2.0107 | AF276239 | P49278 |
| Der p 2.0108 | AF276239 | P49278 |
| Der p 2.0109 | DQ185510 | Q3HWZ3 |
| Der p 2.0110 | DQ185510 | Q3HWZ3 |
| Der p 2.0111 | DQ185510 | Q3HWZ3 |
| Der p 2.0112 | DQ185510 | Q3HWZ3 |
| Der p 2.0113 | DQ185510 | Q3HWZ3 |
| Der p 2.0114 | AM263560 | Q1H8P8 |
| Der p 2.0115 | FM177223 | |

These amino acid and nucleic acid sequences of these isoforms differ from those shown in SEQ ID NO:1-4 by only few substitutions. Therefore, the skilled person can easily provide constructs also on the basis of the isoallergens listed above.

REFERENCES

1. Voorhorst, R., M. I. Spieksma-Boezeman, and F. T. Spieksma. 1964. Is A Mite (*Dermatophagoides* Sp.) The Producer Of The House-Dust Allergen? *Allerg. Asthma (Leipz)* 10:329-334.
2. Platts-Mills, T. A., and M. D. Chapman. 1987. Dust mites: immunology, allergic disease, and environmental control. *J. Allergy Clin. Immunol.* 80:755-775.
3. Boulet, L. P., H. Turcotte, C. Laprise, C. Layertu, P. M. Bedard, A. Lavoie, and J. Hebert. 1997. Comparative degree and type of sensitization to common indoor and outdoor allergens in subjects with allergic rhinitis and/or asthma. *Clin. Exp. Allergy* 27:52-59.
4. Thomas, W. R., W. A. Smith, B. J. Hales, K. L. Mills, and R. M. O'Brien. 2002. Characterization and immunobiology of house dust mite allergens. *Int. Arch. Allergy Immunol.* 129:1-18.
5. Weghofer, M., Y. Dall'Antonia, M. Grote, A. Stocklinger, M. Kneidinger, N. Balic, M. T. Krauth, E. Fernandez-Caldas, W. R. Thomas, M. van Hage, S. Vieths, S. Spitzauer, F. Horak, D. I. Svergun, P. V. Konarev, P. Valent, J. Thalhamer, W. Keller, R. Valenta, and S. Vrtala. 2008. Characterization of Der p 21, a new important allergen derived from the gut of house dust mites. *Allergy* 63:758-767.
6. Pittner, G., S. Vrtala, W. R. Thomas, M. Weghofer, M. Kundi, F. Horak, D. Kraft, and R. Valenta. 2004. Component-resolved diagnosis of house-dust mite allergy with purified natural and recombinant mite allergens. *Clin. Exp. Allergy* 34:597-603.
7. Hales, B. J., A. C. Martin, L. J. Pearce, I. A. Laing, C. M. Hayden, J. Goldblatt, P. N. Le Souef, and W. R. Thomas. 2006. IgE and IgG anti-house dust mite specificities in allergic disease. *J. Allergy Clin. Immunol.* 118:361-367.
8. Chapman, M. D., and T. A. Platts-Mills. 1980. Purification and characterization of the major allergen from *Dermatophagoides pteronyssinus*-antigen P1. *J. Immunol.* 125:587-592.
9. Meyer, C. H., J. F. Bond, M. S. Chen, and M. T. Kasaian. 1994. Comparison of the levels of the major allergens Der p I and Der p II in standardized extracts of the house dust mite, *Dermatophagoides pteronyssinus. Clin. Exp. Allergy* 24:1041-1048.
10. Tovey, E. R., M. D. Chapman, and T. A. Platts-Mills. 1981. Mite faeces are a major source of house dust allergens. *Nature* 289:592-593.
11. Peake, H. L., A. J. Currie, G. A. Stewart, and A. S. McWilliam. 2003. Nitric oxide production by alveolar macrophages in response to house dust mite fecal pellets and the mite allergens, Der p 1 and Der p 2. *J. Allergy Clin. Immunol.* 112:531-537.
12. Durham, S. R., S. M. Walker, E. M. Varga, M. R. Jacobson, F. O'Brien, W. Noble, S. J. Till, Q. A. Hamid, and K. T. Nouri-Aria. 1999. Long-term clinical efficacy of grass-pollen immunotherapy. *N. Engl. J. Med.* 341:468-475.
13. Larche, M., C. A. Akdis, and R. Valenta. 2006. Immunological mechanisms of allergen-specific immunotherapy. *Nat. Rev. Immunol.* 6:761-771.
14. Valenta, R. 2002. The future of antigen-specific immunotherapy of allergy. *Nat. Rev. Immunol.* 2:446-453.
15. Valenta, R., F. Ferreira, M. Focke-Tejkl, B. Linhart, V. Niederberger, I. Swoboda, and S. Vrtala. 2010. From allergen genes to allergy vaccines. *Annu. Rev. Immunol.* 28:211-241.
16. Akdis, M., and C. A. Akdis. 2009. Therapeutic manipulation of immune tolerance in allergic disease. *Nat Rev Drug Discov* 8:645-660.
17. Focke, M., K. Marth, S. Flicker, and R. Valenta. 2008. Heterogeneity of commercial timothy grass pollen extracts. *Clin. Exp. Allergy* 38:1400-1408.
18. Focke, M., K. Marth, and R. Valenta. 2009. Molecular composition and biological activity of commercial birch pollen allergen extracts. *Eur J Clin Invest* 39:429-436.
19. Brunetto, B., R. Tinghino, M. C. Braschi, L. Antonicelli, C. Pini, and P. Iacovacci. Characterization and comparison of commercially available mite extracts for in vivo diagnosis. *Allergy* 65:184-190.
20. Korematsu, S., Y. Tanaka, S. Hosoi, S. Koyanagi, T. Yokota, B. Mikami, and N. Minato. 2000. C8/119S mutation of major mite allergen Derf-2 leads to degenerate secondary structure and molecular polymerization and induces potent and exclusive Th1 cell differentiation. *J. Immunol.* 165:2895-2902.
21. Nakazawa, T., T. Takai, H. Hatanaka, E. Mizuuchi, T. Nagamune, K. Okumura, and H. Ogawa. 2005. Multiple-mutation at a potential ligand-binding region decreased allergenicity of a mite allergen Der f 2 without disrupting global structure. *FEBS Lett.* 579:1988-1994.
22. Smith, A. M., and M. D. Chapman. 1996. Reduction in IgE binding to allergen variants generated by site-directed mutagenesis: contribution of disulfide bonds to the antigenic structure of the major house dust mite allergen Der p 2. *Mol. Immunol.* 33:399-405.

23. Takai, T., S. Ichikawa, H. Hatanaka, F. Inagaki, and Y. Okumura. 2000. Effects of proline mutations in the major house dust mite allergen Der f 2 on IgE-binding and histamine-releasing activity. *Eur. J. Biochem.* 267:6650-6656.

24. Takai, T., A. Mori, T. Yuuki, H. Okudaira, and Y. Okumura. 1999. Non-anaphylactic combination of partially deleted fragments of the major house dust mite allergen Der f 2 for allergen-specific immunotherapy. *Mol. Immunol.* 36:1055-1065.

25. Takai, T., T. Yokota, M. Yasue, C. Nishiyama, T. Yuuki, A. Mori, H. Okudaira, and Y. Okumura. 1997. Engineering of the major house dust mite allergen Der f 2 for allergen-specific immunotherapy. *Nat. Biotechnol.* 15:754-758.

26. Chen, K., G. Fuchs, K. Sonneck, A. Gieras, I. Swoboda, N. Douladiris, B. Linhart, M. Jankovic, T. Pavkov, W. Keller, N. G. Papadopoulos, P. Valent, R. Valenta, and S. Vrtala. 2008. Reduction of the in vivo allergenicity of Der p 2, the major house-dust mite allergen, by genetic engineering. *Mol. Immunol.* 45:2486-2498.

27. Walgraffe, D., C. Matteotti, M. E I Bakkoury, L. Garcia, C. Marchand, D. Bullens, M. Vandenbranden, and A. Jacquet. 2009. A hypoallergenic variant of Der p 1 as a candidate for mite allergy vaccines. *J. Allergy Clin. Immunol.* 123:1150-1156.

28. Suzuki, K., O. Kaminuma, L. Yang, Y. Motoi, T. Takai, S. Ichikawa, K. Okumura, H. Ogawa, A. Mori, F. Takaiwa, and T. Hiroi. 2009. Development of transgenic rice expressing mite antigen for a new concept of immunotherapy. *Int. Arch. Allergy Immunol.* 149 Suppl 1:21-24.

29. Taketomi, E. A., D. A. Silva, M. C. Sopelete, A. M. Gervasio, R. Alves, and S. J. Sung. 2006. Differential IgE reactivity to Der p 1 and Der p 2 allergens of *Dermatophagoides pteronyssinus* in mite-sensitized patients. *J. Investig. Allergol. Clin. Immunol.* 16:104-109.

30. Linhart, B., B. Jahn-Schmid, P. Verdino, W. Keller, C. Ebner, D. Kraft, and R. Valenta. 2002. Combination vaccines for the treatment of grass pollen allergy consisting of genetically engineered hybrid molecules with increased immunogenicity. *Faseb J.* 16:1301-1303.

31. Linhart, B., A. Hartl, B. Jahn-Schmid, P. Verdino, W. Keller, M. T. Krauth, P. Valent, F. Horak, U. Wiedermann, J. Thalhamer, C. Ebner, D. Kraft, and R. Valenta. 2005. A hybrid molecule resembling the epitope spectrum of grass pollen for allergy vaccination. *J. Allergy Clin. Immunol.* 115:1010-1016.

32. Hauswirth, A. W., S. Natter, M. Ghannadan, Y. Majlesi, G. H. Schernthaner, W. R. Sperr, H. J. Buhring, R. Valenta, and P. Valent. 2002. Recombinant allergens promote expression of CD203c on basophils in sensitized individuals. *J. Allergy Clin. Immunol.* 110:102-109.

33. Swoboda, I., A. Bugajska-Schretter, P. Verdino, W. Keller, W. R. Sperr, P. Valent, R. Valenta, and S. Spitzauer. 2002. Recombinant carp parvalbumin, the major cross-reactive fish allergen: a tool for diagnosis and therapy of fish allergy. *J. Immunol.* 168:4576-4584.

The invention claimed is:

1. A polypeptide comprising the amino acid sequence shown in SEQ ID NO:9.

2. The polypeptide of claim 1, wherein said polypeptide comprises a structure selected from the group consisting of:

(I) Met-X-tag, (II) Met-X, (III) X-tag, (IV) Met-tag-X, (V) tag-X, (VI) tag-X-tag, (VII) X, and (VIII) Met-tag-X-tag, wherein X is the amino acid sequence shown in SEQ ID NO:9, Met is methionine, and tag is a peptide tag sequence.

3. The polypeptide of claim 2, wherein said polypeptide consists of the structure X-tag.

4. The polypeptide of claim 2, wherein the tag consists of the amino acid sequence shown in SEQ ID NO:11.

5. The polypeptide of claim 1, wherein said polypeptide comprises the amino acid sequence shown in SEQ ID NO:7.

6. The polypeptide of claim 5, wherein said polypeptide consists of the amino acid sequence shown in SEQ ID NO:7.

7. The polypeptide of claim 1, wherein said polypeptide has an allergenic activity that is lower than the allergenic activity of wild type Der p 2.

8. The polypeptide of claim 1, wherein said polypeptide is formulated for use in the treatment of an allergic disorder.

9. The polypeptide according to claim 8, wherein the allergic disorder is allergy to house dust mites.

10. A polynucleotide encoding the polypeptide of claim 1.

11. The polynucleotide of claim 10, wherein said polypeptide is encoded by the nucleic acid sequence shown in SEQ ID NO:8 or 10.

12. A vector or plasmid comprising the polynucleotide of claim 10.

13. A pharmaceutical composition comprising (i) the polypeptide of claim 1, (ii) a polynucleotide encoding said polypeptide, or (iii) a vector or plasmid comprising said polynucleotide; in combination with a pharmaceutically acceptable diluent or excipient.

14. An immunotherapeutic pharmaceutical composition comprising (i) the polypeptide of claim 1, (ii) a polynucleotide encoding said polypeptide, or (iii) a vector or plasmid comprising said polynucleotide; in combination with an optional adjuvant.

15. A culture comprising a host cell comprising the polynucleotide of claim 10, or a vector or plasmid comprising said polynucleotide.

* * * * *

SEQUENCE LISTING

```
<160> NUMBER OF SEQ ID NOS: 11

<210> SEQ ID NO 1
<211> LENGTH: 223
<212> TYPE: PRT
<213> ORGANISM: Dermatophagoides pteronyssinus

<400> SEQUENCE: 1

Met Thr Asn Ala Cys Ser Ile Asn Gly Asn Ala Pro Ala Glu Ile Asp
1               5                   10                  15

Leu Arg Gln Met Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

Leu Ala Tyr Arg Asn Gln Ser Leu Asp Leu Ala Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
                85                  90                  95

Tyr Val Ala Arg Glu Gln Ser Cys Arg Arg Pro Asn Ala Gln Arg Phe
            100                 105                 110

Gly Ile Ser Asn Tyr Cys Gln Ile Tyr Pro Pro Asn Val Asn Lys Ile
        115                 120                 125

Arg Glu Ala Leu Ala Gln Thr His Ser Ala Ile Ala Val Ile Ile Gly
    130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
                165                 170                 175
```

-continued

```
Gly Tyr Ser Asn Ala Gln Gly Val Asp Tyr Trp Ile Val Arg Asn Ser
            180                 185                 190

Trp Asp Thr Asn Trp Gly Asp Asn Gly Tyr Gly Tyr Phe Ala Ala Asn
        195                 200                 205

Ile Asp Leu Met Met Ile Glu Glu Tyr Pro Tyr Val Val Ile Leu
    210                 215                 220


<210> SEQ ID NO 2
<211> LENGTH: 137
<212> TYPE: PRT
<213> ORGANISM: Dermatophagoides pteronyssinus

<400> SEQUENCE: 2

His Met Asp Gln Val Asp Val Lys Asp Cys Ala Asn His Glu Ile Lys
1               5                   10                  15

Lys Val Leu Val Pro Gly Cys His Gly Ser Glu Pro Cys Ile Ile His
            20                  25                  30

Arg Gly Lys Pro Phe Gln Leu Glu Ala Val Phe Glu Ala Asn Gln Asn
        35                  40                  45

Ser Lys Thr Ala Lys Ile Glu Ile Lys Ala Ser Ile Glu Gly Leu Glu
    50                  55                  60

Val Asp Val Pro Gly Ile Asp Pro Asn Ala Cys His Tyr Met Lys Cys
65                  70                  75                  80

Pro Leu Val Lys Gly Gln Gln Tyr Asp Ile Lys Tyr Thr Trp Ile Val
                85                  90                  95

Pro Lys Ile Ala Pro Lys Ser Glu Asn Val Val Val Thr Val Lys Val
            100                 105                 110

Met Gly Asp Asn Gly Val Leu Ala Cys Ala Ile Ala Thr His Ala Lys
        115                 120                 125

Ile Arg Asp His His His His His His
    130                 135


<210> SEQ ID NO 3
<211> LENGTH: 672
<212> TYPE: DNA
<213> ORGANISM: Dermatophagoides pteronyssinus

<400> SEQUENCE: 3

atgaccaacg cttgctctat caacggtaac gctccggctg aaatcgacct gcgtcagatg      60

cgtaccgtta ccccgatccg tatgcagggt ggttgcggtt cttgctgggc tttctctggt     120

gttgctgcta ccgaatctgc ttacctggct taccgtaacc agtctctgga cctggctgaa     180

caggaactgg ttgactgcgc ttctcagcac ggttgccacg gtgacaccat cccgcgtggt     240

atcgaataca tccagcacaa cggtgttgtt caggaatctt actaccgtta cgttgctcgt     300

gaacagtctt gccgtcgtcc gaacgctcag cgtttcggta tctctaacta ctgccagatc     360

tacccgccga acgttaacaa aatccgtgaa gctctggctc agacccactc tgctatcgct     420

gttatcatcg gtatcaaaga cctggacgct ttccgtcact acgacggtcg taccatcatc     480

cagcgtgaca acggttacca gccgaactac cacgctgtta acatcgttgg ttactctaac     540

gctcagggtg ttgactactg gatcgttcgt aactcttggg acaccaactg gggtgacaac     600

ggttacggtt acttcgctgc taacatcgac ctgatgatga tcgaagaata cccgtacgtt     660

gttatcctgt aa                                                         672


<210> SEQ ID NO 4
<211> LENGTH: 414
```

<212> TYPE: DNA
<213> ORGANISM: Dermatophagoides pteronyssinus

<400> SEQUENCE: 4

```
catatggatc aagtcgatgt caaagattgt gccaatcatg aaatcaaaaa agttttggta     60

ccaggatgcc atggttcaga accatgtatc attcatcgtg gtaaaccatt ccaattggaa    120

gccgttttcg aagccaacca aaactcaaaa accgctaaaa ttgaaatcaa agcttcaatc    180

gaaggtttag aagttgatgt tcccggtatc gatccaaatg catgccatta tatgaaatgt    240

ccattggtta aaggacaaca atatgatatt aaatatacat ggattgttcc aaaaattgca    300

ccaaaatctg aaaatgttgt cgtcactgtt aaagttatgg gtgataatgg tgttttggct    360

tgtgctattg ctactcatgc taaaatccgc gatcatcacc atcaccatca ctaa          414
```

<210> SEQ ID NO 5
<211> LENGTH: 357
<212> TYPE: PRT
<213> ORGANISM: Artificial Sequence
<220> FEATURE:
<223> OTHER INFORMATION: construct Dp 2/1C

<400> SEQUENCE: 5

```
Ile Lys Asp Leu Asp Ala Phe Arg His Tyr Asp Gly Arg Thr Ile Ile
1               5                   10                  15

Gln Arg Asp Asn Gly Tyr Gln Pro Asn Tyr His Ala Val Asn Ile Val
            20                  25                  30

Gly Tyr Ser Asn Ala Gln Gly Val Asp Tyr Trp Ile Val Arg Asn Ser
        35                  40                  45

Trp Asp Thr Asn Trp Gly Asp Asn Gly Tyr Gly Tyr Phe Ala Ala Asn
    50                  55                  60

Ile Asp Leu Met Met Ile Glu Glu Tyr Pro Tyr Val Val Ile Leu Ile
65                  70                  75                  80

Lys Ala Ser Ile Glu Gly Leu Glu Val Asp Val Pro Gly Ile Asp Pro
                85                  90                  95

Asn Ala Cys His Tyr Met Lys Cys Pro Leu Val Lys Gly Gln Gln Tyr
            100                 105                 110

Asp Ile Lys Tyr Thr Trp Ile Val Pro Lys Ile Ala Pro Lys Ser Glu
        115                 120                 125

Asn Val Val Val Thr Val Lys Val Met Gly Asp Asn Gly Val Leu Ala
    130                 135                 140

Cys Ala Ile Ala Thr His Ala Lys Ile Arg Asp His Asn Gly Val Val
145                 150                 155                 160

Gln Glu Ser Tyr Tyr Arg Tyr Val Ala Arg Glu Gln Ser Cys Arg Arg
                165                 170                 175

Pro Asn Ala Gln Arg Phe Gly Ile Ser Asn Tyr Cys Gln Ile Tyr Pro
            180                 185                 190

Pro Asn Val Asn Lys Ile Arg Glu Ala Leu Ala Gln Thr His Ser Ala
        195                 200                 205

Ile Ala Val Ile Ile Gly Asp Gln Val Asp Val Lys Asp Cys Ala Asn
    210                 215                 220

His Glu Ile Lys Lys Val Leu Val Pro Gly Cys His Gly Ser Glu Pro
225                 230                 235                 240

Cys Ile Ile His Arg Gly Lys Pro Phe Gln Leu Glu Ala Val Phe Glu
                245                 250                 255

Ala Asn Gln Asn Ser Lys Thr Ala Lys Ile Glu Thr Asn Ala Cys Ser
            260                 265                 270
```

```
Ile Asn Gly Asn Ala Pro Ala Glu Ile Asp Leu Arg Gln Met Arg Thr
        275                 280                 285

Val Thr Pro Ile Arg Met Gln Gly Gly Cys Gly Ser Cys Trp Ala Phe
    290                 295                 300

Ser Gly Val Ala Ala Thr Glu Ser Ala Tyr Leu Ala Tyr Arg Asn Gln
305                 310                 315                 320

Ser Leu Asp Leu Ala Glu Gln Glu Leu Val Asp Cys Ala Ser Gln His
                325                 330                 335

Gly Cys His Gly Asp Thr Ile Pro Arg Gly Ile Glu Tyr Ile Gln His
            340                 345                 350

His His His His His
        355


<210> SEQ ID NO 6
<211> LENGTH: 1086
<212> TYPE: DNA
<213> ORGANISM: Artificial Sequence
<220> FEATURE:
<223> OTHER INFORMATION: construct Dp 2/1C

<400> SEQUENCE: 6

catatgatca aagacctgga cgctttccgt cactacgacg gtcgtaccat catccagcgt      60

gacaacggtt accagccgaa ctaccacgct gttaacatcg ttggttactc taacgctcag     120

ggtgttgact actggatcgt tcgtaactct tgggacacca actggggtga caacggttac     180

ggttacttcg ctgctaacat cgacctgatg atgatcgaag aatacccgta cgttgttatc     240

ctgatcaaag cttctatcga aggtctggaa gttgacgttc cgggtatcga cccgaacgct     300

tgccactaca tgaaatgccc gctggttaaa ggtcagcagt acgacatcaa atacacctgg     360

atcgttccga aaatcgctcc gaaatctgaa aacgttgttg ttaccgttaa agttatgggt     420

gacaacggtg ttctggcttg cgctatcgct acccacgcta aaatccgtga ccacaacggt     480

gttgttcagg aatcttacta ccgttacgtt gctcgtgaac agtcttgccg tcgtccgaac     540

gctcagcgtt tcggtatctc taactactgc cagatctacc cgccgaacgt taacaaaatc     600

cgtgaagctc tggctcagac ccactctgct atcgctgtta tcatcggtga ccaggttgac     660

gttaaagact gcgctaacca cgaaatcaaa aaagttctgg ttccgggttg ccacggttct     720

gaaccgtgca tcatccaccg tggtaaaccg ttccagctgg aagctgtttt cgaagctaac     780

cagaactcta aaaccgctaa aatcgaaacc aacgcttgct ctatcaacgg taacgctccg     840

gctgaaatcg acctgcgtca gatgcgtacc gttaccccga tccgtatgca gggtggttgc     900

ggttcttgct gggctttctc tggtgttgct gctaccgaat ctgcttacct ggcttaccgt     960

aaccagtctc tggacctggc tgaacaggaa ctggttgact gcgcttctca gcacggttgc    1020

cacggtgaca ccatcccgcg tggtatcgaa tacatccagc accaccacca ccaccactaa    1080

gaattc                                                               1086


<210> SEQ ID NO 7
<211> LENGTH: 357
<212> TYPE: PRT
<213> ORGANISM: Artificial Sequence
<220> FEATURE:
<223> OTHER INFORMATION: construct Dp 2/1S

<400> SEQUENCE: 7

Ile Lys Asp Leu Asp Ala Phe Arg His Tyr Asp Gly Arg Thr Ile Ile
1               5                   10                  15
```

-continued

```
Gln Arg Asp Asn Gly Tyr Gln Pro Asn Tyr His Ala Val Asn Ile Val
            20                  25                  30

Gly Tyr Ser Asn Ala Gln Gly Val Asp Tyr Trp Ile Val Arg Asn Ser
        35                  40                  45

Trp Asp Thr Asn Trp Gly Asp Asn Gly Tyr Gly Tyr Phe Ala Ala Asn
    50                  55                  60

Ile Asp Leu Met Met Ile Glu Glu Tyr Pro Tyr Val Val Ile Leu Ile
65                  70                  75                  80

Lys Ala Ser Ile Glu Gly Leu Glu Val Asp Val Pro Gly Ile Asp Pro
                85                  90                  95

Asn Ala Ser His Tyr Met Lys Ser Pro Leu Val Lys Gly Gln Gln Tyr
            100                 105                 110

Asp Ile Lys Tyr Thr Trp Ile Val Pro Lys Ile Ala Pro Lys Ser Glu
        115                 120                 125

Asn Val Val Val Thr Val Lys Val Met Gly Asp Asn Gly Val Leu Ala
    130                 135                 140

Ser Ala Ile Ala Thr His Ala Lys Ile Arg Asp His Asn Gly Val Val
145                 150                 155                 160

Gln Glu Ser Tyr Tyr Arg Tyr Val Ala Arg Glu Gln Ser Ser Arg Arg
                165                 170                 175

Pro Asn Ala Gln Arg Phe Gly Ile Ser Asn Tyr Ser Gln Ile Tyr Pro
            180                 185                 190

Pro Asn Val Asn Lys Ile Arg Glu Ala Leu Ala Gln Thr His Ser Ala
        195                 200                 205

Ile Ala Val Ile Ile Gly Asp Gln Val Asp Val Lys Asp Ser Ala Asn
    210                 215                 220

His Glu Ile Lys Lys Val Leu Val Pro Gly Ser His Gly Ser Glu Pro
225                 230                 235                 240

Ser Ile Ile His Arg Gly Lys Pro Phe Gln Leu Glu Ala Val Phe Glu
                245                 250                 255

Ala Asn Gln Asn Ser Lys Thr Ala Lys Ile Glu Thr Asn Ala Ser Ser
            260                 265                 270

Ile Asn Gly Asn Ala Pro Ala Glu Ile Asp Leu Arg Gln Met Arg Thr
        275                 280                 285

Val Thr Pro Ile Arg Met Gln Gly Gly Ser Gly Ser Ser Trp Ala Phe
    290                 295                 300

Ser Gly Val Ala Ala Thr Glu Ser Ala Tyr Leu Ala Tyr Arg Asn Gln
305                 310                 315                 320

Ser Leu Asp Leu Ala Glu Gln Glu Leu Val Asp Ser Ala Ser Gln His
                325                 330                 335

Gly Ser His Gly Asp Thr Ile Pro Arg Gly Ile Glu Tyr Ile Gln His
            340                 345                 350

His His His His His
        355
```

<210> SEQ ID NO 8
<211> LENGTH: 1086
<212> TYPE: DNA
<213> ORGANISM: Artificial Sequence
<220> FEATURE:
<223> OTHER INFORMATION: construct Dp 2/1S

<400> SEQUENCE: 8

```
catatgatca aagacctgga cgctttccgt cactacgacg gtcgtaccat catccagcgt      60
```

-continued

```
gacaacggtt accagccgaa ctaccacgct gttaacatcg ttggttactc taacgctcag    120

ggtgttgact actggatcgt tcgtaactct tgggacacca actggggtga caacggttac    180

ggttacttcg ctgctaacat cgacctgatg atgatcgaag aatacccgta cgttgttatc    240

ctgatcaaag cttctatcga aggtctggaa gttgacgttc cgggtatcga cccgaacgct    300

tctcactaca tgaaatctcc gctggttaaa ggtcagcagt acgacatcaa atacacctgg    360

atcgttccga aaatcgctcc gaaatctgaa aacgttgttg ttaccgttaa agttatgggt    420

gacaacggtg ttctggcttc tgctatcgct acccacgcta aaatccgtga ccacaacggt    480

gttgttcagg aatcttacta ccgttacgtt gctcgtgaac agtcttctcg tcgtccgaac    540

gctcagcgtt tcggtatctc taactactct cagatctacc cgccgaacgt taacaaaatc    600

cgtgaagctc tggctcagac ccactctgct atcgctgtta tcatcggtga ccaggttgac    660

gttaaagact ctgctaacca cgaaatcaaa aaagttctgg ttccgggttc tcacggttct    720

gaaccgtcta tcatccaccg tggtaaaccg ttccagctgg aagctgtttt cgaagctaac    780

cagaactcta aaaccgctaa aatcgaaacc aacgcttctt ctatcaacgg taacgctccg    840

gctgaaatcg acctgcgtca gatgcgtacc gttaccccga tccgtatgca gggtggttct    900

ggttcttctt gggctttctc tggtgttgct gctaccgaat ctgcttacct ggcttaccgt    960

aaccagtctc tggacctggc tgaacaggaa ctggttgact ctgcttctca gcacggttct   1020

cacggtgaca ccatcccgcg tggtatcgaa tacatccagc accaccacca ccaccactaa   1080

gaattc                                                              1086


<210> SEQ ID NO 9
<211> LENGTH: 351
<212> TYPE: PRT
<213> ORGANISM: Artificial Sequence
<220> FEATURE:
<223> OTHER INFORMATION: construct Dp 2/1S without C-terminal (His)6

<400> SEQUENCE: 9

Ile Lys Asp Leu Asp Ala Phe Arg His Tyr Asp Gly Arg Thr Ile Ile
1               5                   10                  15

Gln Arg Asp Asn Gly Tyr Gln Pro Asn Tyr His Ala Val Asn Ile Val
            20                  25                  30

Gly Tyr Ser Asn Ala Gln Gly Val Asp Tyr Trp Ile Val Arg Asn Ser
        35                  40                  45

Trp Asp Thr Asn Trp Gly Asp Asn Gly Tyr Gly Tyr Phe Ala Ala Asn
    50                  55                  60

Ile Asp Leu Met Met Ile Glu Glu Tyr Pro Tyr Val Val Ile Leu Ile
65                  70                  75                  80

Lys Ala Ser Ile Glu Gly Leu Glu Val Asp Val Pro Gly Ile Asp Pro
                85                  90                  95

Asn Ala Ser His Tyr Met Lys Ser Pro Leu Val Lys Gly Gln Gln Tyr
            100                 105                 110

Asp Ile Lys Tyr Thr Trp Ile Val Pro Lys Ile Ala Pro Lys Ser Glu
        115                 120                 125

Asn Val Val Val Thr Val Lys Val Met Gly Asp Asn Gly Val Leu Ala
    130                 135                 140

Ser Ala Ile Ala Thr His Ala Lys Ile Arg Asp His Asn Gly Val Val
145                 150                 155                 160

Gln Glu Ser Tyr Tyr Arg Tyr Val Ala Arg Glu Gln Ser Ser Arg Arg
                165                 170                 175
```

```
Pro Asn Ala Gln Arg Phe Gly Ile Ser Asn Tyr Ser Gln Ile Tyr Pro
            180                 185                 190

Pro Asn Val Asn Lys Ile Arg Glu Ala Leu Ala Gln Thr His Ser Ala
        195                 200                 205

Ile Ala Val Ile Ile Gly Asp Gln Val Asp Val Lys Asp Ser Ala Asn
    210                 215                 220

His Glu Ile Lys Lys Val Leu Val Pro Gly Ser His Gly Ser Glu Pro
225                 230                 235                 240

Ser Ile Ile His Arg Gly Lys Pro Phe Gln Leu Glu Ala Val Phe Glu
                245                 250                 255

Ala Asn Gln Asn Ser Lys Thr Ala Lys Ile Glu Thr Asn Ala Ser Ser
            260                 265                 270

Ile Asn Gly Asn Ala Pro Ala Glu Ile Asp Leu Arg Gln Met Arg Thr
        275                 280                 285

Val Thr Pro Ile Arg Met Gln Gly Gly Ser Gly Ser Ser Trp Ala Phe
    290                 295                 300

Ser Gly Val Ala Ala Thr Glu Ser Ala Tyr Leu Ala Tyr Arg Asn Gln
305                 310                 315                 320

Ser Leu Asp Leu Ala Glu Gln Glu Leu Val Asp Ser Ala Ser Gln His
                325                 330                 335

Gly Ser His Gly Asp Thr Ile Pro Arg Gly Ile Glu Tyr Ile Gln
            340                 345                 350


<210> SEQ ID NO 10
<211> LENGTH: 1053
<212> TYPE: DNA
<213> ORGANISM: Artificial Sequence
<220> FEATURE:
<223> OTHER INFORMATION: construct Dp 2/1S without C-terminal (His)6

<400> SEQUENCE: 10

atcaaagacc tggacgcttt ccgtcactac gacggtcgta ccatcatcca gcgtgacaac      60

ggttaccagc cgaactacca cgctgttaac atcgttggtt actctaacgc tcagggtgtt     120

gactactgga tcgttcgtaa ctcttgggac accaactggg gtgacaacgg ttacggttac     180

ttcgctgcta acatcgacct gatgatgatc gaagaatacc cgtacgttgt tatcctgatc     240

aaagcttcta tcgaaggtct ggaagttgac gttccgggta tcgacccgaa cgcttctcac     300

tacatgaaat ctccgctggt taaaggtcag cagtacgaca tcaaatacac ctggatcgtt     360

ccgaaaatcg ctccgaaatc tgaaaacgtt gttgttaccg ttaaagttat gggtgacaac     420

ggtgttctgg cttctgctat cgctacccac gctaaaatcc gtgaccacaa cggtgttgtt     480

caggaatctt actaccgtta cgttgctcgt gaacagtctt ctcgtcgtcc gaacgctcag     540

cgtttcggta tctctaacta ctctcagatc tacccgccga acgttaacaa aatccgtgaa     600

gctctggctc agacccactc tgctatcgct gttatcatcg gtgaccaggt tgacgttaaa     660

gactctgcta accacgaaat caaaaaagtt ctggttccgg gttctcacgg ttctgaaccg     720

tctatcatcc accgtggtaa accgttccag ctggaagctg ttttcgaagc taaccagaac     780

tctaaaaccg ctaaaatcga aaccaacgct tcttctatca acggtaacgc tccggctgaa     840

atcgacctgc gtcagatgcg taccgttacc ccgatccgta tgcagggtgg ttctggttct     900

tcttgggctt tctctggtgt tgctgctacc gaatctgctt acctggctta ccgtaaccag     960

tctctggacc tggctgaaca ggaactggtt gactctgctt ctcagcacgg ttctcacggt    1020

gacaccatcc cgcgtggtat cgaatacatc cag                                 1053
```

-continued

```
<210> SEQ ID NO 11
<211> LENGTH: 6
<212> TYPE: PRT
<213> ORGANISM: Artificial Sequence
<220> FEATURE:
<223> OTHER INFORMATION: (His)6 tag

<400> SEQUENCE: 11

His His His His His His
1               5
```